United States Patent [19]

Pawlowski et al.

[11] Patent Number: 5,216,158
[45] Date of Patent: Jun. 1, 1993

[54] OXADIAZOLE COMPOUNDS CONTAINING 4,6-BIS-TRICHLOROMETHYL-S-TRIAZIN-2-YL GROUPS, PROCESS FOR THEIR PREPARATION

[75] Inventors: Georg Pawlowski, Wiesbaden; Fritz Erdmann, Eltville; Heidrun Lutz, Mainz, all of Fed. Rep. of Germany

[73] Assignee: Hoechst Aktiengesellschaft, Frankfurt am Main, Fed. Rep. of Germany

[21] Appl. No.: 774,728

[22] Filed: Oct. 8, 1991

Related U.S. Application Data

[63] Continuation of Ser. No. 317,560, Mar. 1, 1989, abandoned.

[30] Foreign Application Priority Data

Mar. 7, 1988 [DE] Fed. Rep. of Germany ....... 3807380

[51] Int. Cl.$^5$ ............................................. C07D 251/24
[52] U.S. Cl. ........................................................ 544/216
[58] Field of Search ........................................ 544/216

[56] References Cited

U.S. PATENT DOCUMENTS

| 3,954,475 | 5/1976 | Bonham et al. ........................ 96/67 |
| 4,040,922 | 8/1977 | Wang et al. ..................... 204/159.15 |
| 4,189,323 | 2/1980 | Buhr ..................................... 430/281 |
| 4,212,970 | 7/1980 | Iwasaki ............................... 542/455 |
| 4,232,106 | 11/1980 | Iwasaki et al. ..................... 430/170 |
| 4,371,606 | 2/1983 | Döngs ................................. 430/281 |
| 4,371,607 | 2/1983 | Dönges ............................... 430/281 |
| 4,619,998 | 10/1986 | Buhr ................................. 544/193.1 |
| 4,696,888 | 9/1987 | Buhr ................................... 430/270 |
| 4,701,399 | 10/1987 | Nagano et al. ...................... 430/179 |

FOREIGN PATENT DOCUMENTS 0135348  3/1985  European Pat. Off. .
84/7165  4/1985  South Africa .

OTHER PUBLICATIONS

R. Huisgen, et al., *Angew. Chem.*, 70, 272 (1958).

Primary Examiner—John M. Ford
Attorney, Agent, or Firm—Foley & Lardner

[57] ABSTRACT

Compounds of general formula I are disclosed

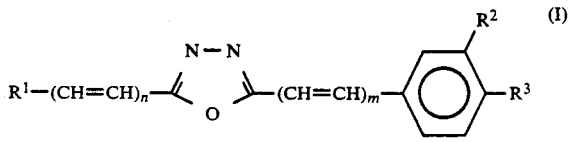

wherein
R$^1$ denotes an unsubstituted or substituted carbocyclic or heterocyclic aryl radical,
R$^2$ and R$^3$ are different from each other and either denote a hydrogen atom or a 4,6-bis-trichloromethyl-s-triazin-2-yl group, and
n and m independently of each other, denote one of the numbers 0 and 1.

The compounds are effective free-radical-forming photoinitiators and photolytically-activatable acid donors for photosensitive compositions.

10 Claims, No Drawings

OXADIAZOLE COMPOUNDS CONTAINING 4,6-BIS-TRICHLOROMETHYL-S-TRIAZIN-2-YL GROUPS, PROCESS FOR THEIR PREPARATION

This application is a continuation of application Ser. No. 07/317,560, filed Mar. 1, 1989, now abandoned.

BACKGROUND OF THE INVENTION

The present invention relates to oxadiazole compounds containing 4,6-bis-trichloromethyl-s-triazin-2-yl groups, to a process for their preparation and to a photosensitive composition containing these compounds.

It is known to employ aromatic or heterocyclic compounds containing trichloromethyl groups as initiators for various photochemical reactions.

DE-A 22 43 621 discloses s-triazines substituted by one or two trichloromethyl groups and one chromophoric group that are suitable as photoinitiators in photopolymerizable compositions and as acid donors in a mixture with acetals that can be split by acid. These compounds include those that absorb light in the visible region of the electromagnetic spectrum and act as photoinitiators.

Similar compounds, in which an at least binuclear aromatic radical as a chromophoric group is bonded directly to the triazine ring, are disclosed in DE-A 27 18 259 (U.S. Pat. No. 4,189,323).

EP-A 137 452 describes similar 4,6-bis-trichloromethyl-s-triazines having an optionally-substituted styryl group in the 2-position. The absorption peaks of these compounds are mostly in the near ultraviolet region.

DE-A 28 51 472 describes photosensitive compositions containing 2-halogenomethyl-5-vinyl-1,3,4-oxadiazole derivatives as photoinitiators.

Similar compounds that act as photoinitiators are disclosed in DE-A 35 06 274. These compounds have absorption peaks at longer wavelengths.

DE-A 30 21 590 and DE-A 30 21 599 disclose halogenoxazoles substituted by trichloromethylphenyl groups that are suitable as photoinitiators, like the above-mentioned compounds.

Moreover, EP-A 135 348 and EP-A 135 863 disclose 1-alkyl-2-carbonylmethylene-benzothiazoles and similar heterocyclic compounds, carrying a trichloromethylphenyl group on the carbonyl group. These compounds also have a maximum sensitivity in the near ultraviolet region.

The reaction conditions for preparing many of these compounds are fairly drastic resulting in a yield that is relatively low and the formation of undesired by-products that are difficult to separate (for example, DE-A 22 43 621, DE-A 27 18 259 or 28 51 472). With many known initiators, the inadequate sensitivity makes it necessary to combine different initiator systems. It has, moreover, been found that precisely the most sensitive of the known initiators do not have a storage stability which meets the requirements of practical application in photosensitive compositions, in particular in contact with copper surfaces. Most of the known photoinitiators that can also be used as photolytically-activatable acid donors, furthermore, have maximum sensitivities between 380 and 420 nm.

In modern exposure technology, however, two new trends appear, that have opposite directions. On the one hand, for the generation of finer structures and an improved reproduction thereof, in particular in microelectronics, light sources having maximum emissions at shorter wavelengths, e.g., at 365 nm, will be employed to an increasing extent in the future. In the graphic industry, on the other hand, light sources, e.g., lasers, are used in the course of digitization of information, that emit light in the visible region of the electromagnetic spectrum, in general above 450 nm.

SUMMARY OF THE INVENTION

It is therefore an object of the present invention to provide novel photosensitive compounds that can be used in various photosensitive materials, that are relatively readily accessible and that offer a wide range of possible variations in practical use, being adaptable in an optimum manner to the requirements of each of the various fields of application.

It is, in particular, an object of the present invention to provide photosensitive compounds having high sensitivities in the ultraviolet spectral region at about 365 nm such that their activity is initiated even by weak light sources or a reduction of the exposure time is possible.

It is a further object of the present invention to provide photosensitive compositions capable of being sensitized to high sensitivities for the spectral region between 400 and 700 nm, in particular from 450 to 650 nm, by the addition of suitable dyes or sensitizers.

It is another object of the present invention to provide photosensitive compositions used for layers of high thicknesses, in which the photoinitiator does not have a strong inherent coloration to permit a full photoreaction.

It is yet another object of the present invention to provide photosensitive compositions having a high storage stability, irrespective of the material of the support, and that produce a clearly visible image contrast in the photosensitive layer after irradiation.

These and other objects of the present invention are achieved by providing compounds of the general formula I

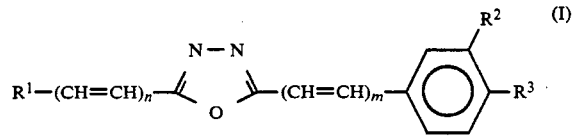

wherein $R^1$ denotes an unsubstituted or substituted carbocyclic or heterocyclic aryl radical, $R^2$ and $R^3$ are different from each other and either denote a hydrogen atom or a 4,6-bis-trichloromethyl-s-triazin-2-yl group, and n and m independently of each other, denote one of the numbers 0 and 1.

The objects of the invention are also achieved by providing a photosensitive composition comprising a photosensitive organic compound (a) having at least one 4,6-bis-trichloromethyl-s-triazin-2-yl substituent and a compound (b) capable of reacting with the photoreaction product of compound (a) to form a product having a light absorption, tackiness or solubility in a developer differing from that of compound (b).

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

The composition of the present invention comprises a compound according to general formula I.

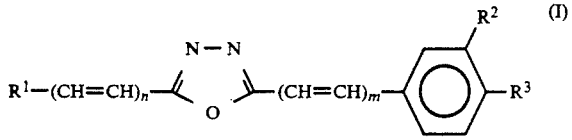

Under the action of actinic radiation, compounds according to the present invention form free radicals capable of initiating chemical reactions, in particular polymerizations initiated by free radicals.

Upon irradiation, the compounds also form hydrogen halide, by means of which acid-catalyzed reactions, for example the cleavage of acetal bonds, or formation of salts, for example color changes of indicator dyes, can be effected.

In formula I, preferably $R^1$ is a phenyl radical and may be substituted by 1 to 3 alkyl, alkoxy, aryl, aryloxyaryl, perhaloalkyl, nitro, cyano, carboxyl, carbonyl or diarylamino groups, a naphthyl radical, a relatively highly aggregated aromatic hydrocarbon radical or a heteroaromatic radical, in particular a mononuclear to trinuclear N-heteroyl radical.

In the case of $R^1$ substituted by alkyl or alkoxy radicals, the latter may, in general, contain 1 to 10, preferably 1 to 6, carbon atoms. They may be unbranched or branched or, if appropriate, cyclized to form a cycloaliphatic radical, for example a cyclohexyl radical.

The compounds of the present invention can advantageously be prepared according to two methods.

A first method, that is not preferred, is illustrated by the following reaction scheme, in which $R^1$, $R^2$, $R^3$, m and n have the above-specified meaning.

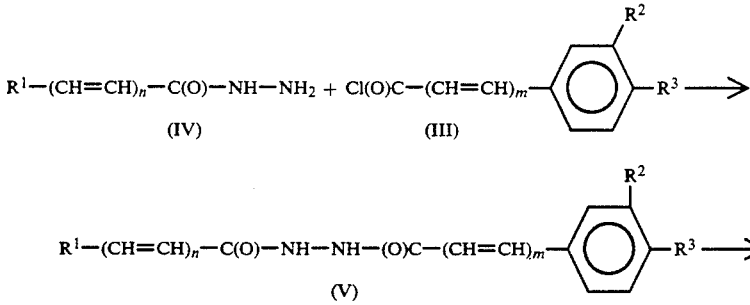

According to this first method acid hydrazides of formula IV can be reacted with acid chlorides of formula III to form bisacylhydrazides of formula V, that are then converted into the compounds of the present invention, corresponding to formula I, by means of a dihydrating agent. The hydrazides can be prepared by known processes, for example, according to W. O. Godtfredsen and S. Vangedal, *Acta Chem. Scand.*, 9, 1498 (1955) or R. Harada and H. Kondo, *Bull. Chem. Soc. Jpn.*, 41, 2521 (1968). Further preparation methods are described in Houben-Weyl *Methoden der Organischen Chemie* [*Methods of Organic Chemistry*], Volume VIII, page 676, et seq. According to known methods as described, for example, in Houben-Weyl, Volume 10/2, page 127, et seq., the hydrazides of formula IV are converted into the bisacylhydrazides of formula V by reacting them with acid chlorides of formula III. The preparation of acid chlorides of formula III is described in application Ser. No. 07/317,562 (corresponding to German Patent Application, No. P 38 07 378.1), filed concurrently herewith. The contents of this copending application are hereby incorporated by reference. Bisacylhydrazides of formula V can be converted into the oxadiazole derivatives of the present invention, corresponding to formula I, in accordance with the method of M. P. Hutt, E. F. Elslager and L. M. Werbel, *J. Heterocycl. Chem.*, 7, 511 (1970).

In a second method, that is preferred, aromatic nitriles of formula VI are reacted with sodium azide, preferably lithium or ammonium azide, and thus converted into corresponding tetrazoles of formula II. This reaction can, for example, be carried out analogously to the direction of W. G. Finnegan, R. A. Henry and R. Loftquist, *J. Amer. Chem. Soc.*, 80, 3908 (1958). Acid chlorides of formula III can then be used for converting tetrazoles of formula II into the compounds of the present invention, corresponding to formula I, in a one-step reaction resulting in a high yield, for example, analogously to the directions of R. Huisgen, J. Sauer and H. J. Sturn, *Angew. Chem.*, 70, 272 (1958):

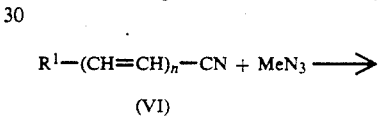

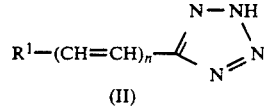

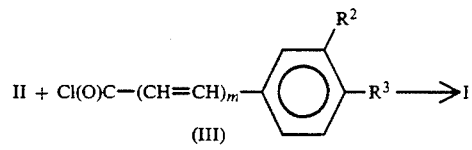

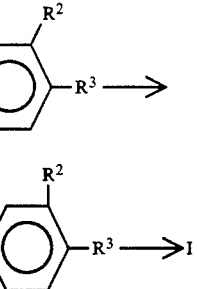

It is actually surprising that the reaction should proceed according to this scheme, since it is known that trichloromethyl groups, particularly when they are linked to a triazine ring, as in the present case, enter extremely easily into nucleophilic substitution reactions, in particular with nucleophilic compounds containing nitrogen. However, the examples described below show that this possible side reaction is virtually unimportant and that the compounds of formula I are obtained in high yields.

Nitriles of general formula VI that can be used include alkyl nitriles and, in particular, aryl or arylethenyl nitriles, and may be substituted by inert radicals that enter into 1,3-dipolar addition reactions only under drastic conditions or not at all. Nitriles of this kind can be prepared according to various known methods.

Conversion into tetrazoles of formula II is appropriately carried out in such a way that the nitrile is allowed to react with about 1 to 5 times, preferably about 2 times, the stoichiometric quantity of an ammonium, lithium or sodium azide in a polar solvent, preferably dimethyl formamide or 2-methoxyethanol, in a temperature range between about 50° and 200° C., preferably between about 100° to 120° C. When sodium azide is used as a reagent, a lithium or ammonium salt, for example, lithium or ammonium chloride, is appropriately added to the mixture, because the intermediately-formed lithium azide has a better solubility in the solvents used in the process. The reaction mixture is maintained at the predetermined temperature for about 5 to 100 hours, preferably about 20 to 30 hours and, after cooling, the mixture is poured into water. After carefully acidifying with an aqueous hydrochloric acid and, if appropriate, after sufficient cooling, the tetrazole of formula II is deposited in high purity and high yield and can be isolated by filtering. Failing a quantitative reaction, non-reacted nitrile can be removed by filtering or extracting the aqueous, nonacidified solution with an organic solvent, for example, ether or dichloromethane.

The tetrazoles are converted into the oxadiazole derivatives of the invention, corresponding to formula I, by dissolving or suspending them in about 5 to 50 times the quantity of a base, preferably pyridine. The acid chloride of general formula III is added to this mixture, which should be cooled in the process, if required. The mixture is then slowly heated to about 50° to 150° C., preferably about 80° to 120° C., and a vigorously starting nitrogen evolution is observed. After about 1 to 5 hours, preferably after about 2 to 3 hours, provided the evolution of nitrogen has come to an end, the mixture is allowed to cool and is poured into water. In the process, the oxadiazole derivative of the invention, corresponding to formula I, is generally obtained in high purity. If required, the aqueous solution can be acidified and/or extracted with an organic solvent. In this event, the product is isolated by evaporating the solvent. The compounds of the present invention are optionally further purified by recrystallizing.

The compounds according to the invention are suitable as photoinitiators for photopolymerizable compositions containing polymerizable compounds, initiators and optionally binders as the essential constituents.

The polymerizable compounds employed in the photosensitive compositions according to the present invention contain at least one ethylenic double bond and can be present in the form of monomers, oligomers, polymers or mixtures of these components. Examples of suitable compounds are optionally polyunsaturated carboxylic acids and the salts thereof, acid derivatives such as esters or amides, derivatives obtained from carbonic acid, for example, urethanes, sulfonyl urethanes or phosphinyl urethanes or the corresponding urea compounds, unsaturated ethers and unsaturated derivatives obtainable from epoxides.

Examples of carboxylic acids are acrylic acid, methacrylic acid, itaconic acid, crotonic acid, isocrotonic acid, and maleic acid. Examples of salts of carboxylic acids are the sodium and potassium salts of the aforementioned carboxylic acids.

Suitable esters of unsaturated carboxylic acids with optionally polyhydric alcohols include the esters of acrylic and methacrylic acids, such as ethylene glycol di(meth)acrylate, triethyleneglycol di(meth)acrylate, 1,3-butanediol di(meth)acrylate, tetramethylenediol di(meth)acrylate, propylene glycol di(meth)acrylate, trimethylolpropane tri(meth)acrylate, trimethylolethane tri(meth)acrylate, 1,4-cyclohexanediol di(meth)acrylate, tetraethyleneglycol di(meth)acrylate, pentaerythritol di(meth)acrylate, pentaerythritol tri(meth)acrylate, pentaerythritol tetra(meth)acrylate, dipentaerythritol di(meth)acrylate, dipentaerythritol tetra(meth)acrylate, sorbitol tri(meth)acrylate, sorbitol tetra(meth)acrylate, sorbitol penta(meth)acrylate, sorbitol hexa(meth)acrylate, and polyester(meth)acrylate oligomers, 2,2-bis-[p-(3-(meth)acryloyloxy-2-hydroxypropoxy)-phenyl]-propane and 2,2-bis-[4-(meth)acryloyloxy ethoxy-phenyl]propane; esters of itaconic acid, such as ethylene glycol diitaconate, propyleneglycol diitaconate, 1,3-butanediol diitaconate, 1,4-butanediol diitaconate, tetramethylenediol diitaconate, pentaerythritol diitaconate and sorbitol tetraitaconate; esters of crotonic acid, such as ethylene glycol dicrotonate, tetramethylenediol dicrotonate, pentaerythritol dicrotonate and sorbitol tetracrotonate; esters of isocrotonic acid, such as ethylene glycol diisocrotonate, pentaerythritol diisocrotonate and sorbitol tetraisocrotonate; and esters of maleic acid, such as ethylene glycol dimaleinate, triethyleneglycol dimaleinate, pentaerythritol dimaleinate and sorbitol tetramaleinate. These esters can be used individually or as mixtures.

Amides of unsaturated carboxylic acids with optionally polyvalent amines that can be used comprise acrylamides and methacrylamides, for example, methylene-bis-(meth)acrylamide, 1,6-hexamethylene-bis-(meth)acrylamide, diethylene-triamine-tris-(meth)acrylamide and xylylene-bis(meth)acrylamide.

Further advantageously used polymerizable compounds containing an ethylenically unsaturated bond comprise vinyl-urethane compounds having at least two polymerizable vinyl groups in the molecule, obtained by the addition reaction of a hydroxy alkyl(meth)acrylate, for example, hydroxyethylmethacrylate or 2-hydroxy-propylacrylate, with an isocyanate having at least two isocyanate groups in the molecule, or those obtained by addition reaction from an isocyanatoalkyl(meth)acrylate, for example, 2-isocyanatoethylmethacrylate, and a polyhydric alcohol which may contain nitrogen atoms.

Of the above-specified compounds, the acrylic and methacrylic esters of polyhydric alcohols and the reaction products of diisocyanates with partial esters of polyhydric unsaturated alcohols, and the reaction products of hydroxyalkyl(meth)acrylates with polyisocyanates and isocyanatoalkyl(meth)acrylates with polyalcohols represent particularly preferred polymerizable components. Examples of the last-mentioned monomers are described in DE-A 20 64 079, DE-A 23 61 041 and DE-A 28 22 190. The amount of monomers in the layer is, in general, about 10% to 80% by weight, preferably about 20% to 60% by weight, based on the amount of non-volatile constituents.

When the photoinitiators according to the present invention are used in photopolymerizable compositions, the latter may also contain a binder. The binder must be compatible with the ethylenically unsaturated polymerizable compound and with the photoinitiator of the invention. After the imagewise exposure it must be possible to process the photosensitive layer by washing out or peel apart. Moreover, the binder should impart sufficient toughness, strength, abrasion resistance and flexibility to the photosensitive layer. The binder usually comprises a linear organic polymer.

Binders that may be used include, for example, chlorinated polyethylene, chlorinated polypropylene, polyalkyl(meth)acrylates, in which the alkyl group is, for example, methyl, ethyl, n-butyl, i-butyl, n-hexyl or 2-ethylhexyl, copolymers of the alkyl(meth)acrylates mentioned with at least one monomer, such as acrylonitrile, vinyl chloride, vinylidene chloride, styrene or butadiene; polyvinyl chloride, vinyl chloride/acrylonitrile copolymers, polyvinylidene chloride, vinylidene chloride/acrylonitrile copolymers, polyvinyl acetate, polyvinyl alcohol, polyacrylonitrile, acrylonitrile/styrene copolymers, acrylonitrile/butadiene/styrene copolymers, polystyrene, polymethylstyrene, polyamides (e.g., Nylon-6), polyurethanes, methyl cellulose, ethyl cellulose, acetyl cellulose, polyvinylformal, and polyvinylbutyral.

Binders that are insoluble in water and soluble in organic solvents and soluble or at least swellable in aqueous-alkaline solutions are particularly suitable.

Especially mentioned are binders containing carboxyl groups, for example, copolymers of (meth)acrylic acid and/or the unsaturated homologs thereof, such as crotonic acid, copolymers of maleic anhydride or the half-esters thereof, reaction products of polymers containing hydroxyl groups with dicarboxylic acid anhydrides and mixtures thereof.

Other suitable binders include reaction products of polymers carrying groups containing acidic hydrogen, all or some of which have been reacted with activated isocyanates, for example, reaction products of polymers containing hydroxyl groups with aliphatic or aromatic sulfonyl isocyanates or phosphinic acid isocyanates.

Further suitable binders include polymers containing hydroxyl groups, for example, copolymers of hydroxyalkyl(meth)acrylates, copolymers of allyl alcohol, copolymers of vinyl alcohol, polyurethanes or polyesters, as well as epoxy resins, provided these contain a sufficient number of free OH groups or are modified in such a way that they are soluble in aqueous-alkaline solutions, or polymers containing phenolic hydroxyl groups, for example, condensation products of condensible carbonyl compounds, in particular, formaldehyde, acetaldehyde or acetone, with phenols; or copolymers of hydroxystyrenes. It is also possible to use copolymers of (meth)acrylic acid amide with alkyl(meth)acrylates.

The above-described polymers are, in particular, suitable when they have a molecular weight between 500 and 200,000 or above, preferably 1,000 to 100,000, and either have acid numbers between 10 and 250, preferably 20 to 200, or hydroxyl numbers between 50 and 750, preferably 100 to 500.

Preferred alkali-soluble binders include copolymers of (meth)acrylic acid with alkyl (meth)acrylates, (meth)acrylic acid nitrile or the like; copolymers of crotonic acid with alkyl(meth)acrylates, (meth)acrylic acid nitrile or the like; copolymers of vinyl acetic acid with alkyl(meth)acrylates; copolymers of maleic anhydride with optionally substituted styrenes, unsaturated hydrocarbons, unsaturated ethers or esters; esterification products of the copolymers of maleic anhydride; esterification products of polymers containing hydroxyl groups with anhydrides of dicarboxylic acids or polycarboxylic acids, copolymers of hydroxyalkyl(meth)acrylates with alkyl(meth)acrylates, (meth)acrylic acid nitrile and the like; copolymers of allyl alcohol with optionally substituted styrenes; copolymers of vinyl alcohol with alkyl(meth)acrylates or other unsaturated compounds which are capable of polymerizing; polyurethanes, provided they have a sufficient number of free OH groups; epoxy resins; polyesters; partially saponified vinyl acetate copolymers; polyvinyl acetals having free OH groups; copolymers of hydroxystyrenes with alkyl(meth)acrylates or the like; phenol/formaldehyde resins, e.g., novolaks.

The amount of binder in the photosensitive layer comprises, in general, about 20% to 90% by weight, preferably about 40% to 80% by weight.

The photoinitiators according to the present invention are added to compositions of this type in amounts ranging between about 0.1% and 15.0% by weight, preferably between about 0.2% to 5% by weight.

Depending on the intended use and depending on the desired properties, the photopolymerizable compositions can comprise various substances as additives, e.g., inhibitors to prevent thermal polymerization, hydrogen donors, substances which regulate the spectral sensitivity, dyes, colored and colorless pigments, color precursors, indicators and plasticizers.

Inhibitors that can be used comprise, for example, hydroquinone, p-methoxyphenol, di-t-butyl-p-cresol, pyrogallol, t-butyl-pyrocatechol, benzoquinone, cuprous chloride, phenothiazine, chloranil, naphthylamine, naphthol, nitrobenzene, and dinitrobenzene.

Suitable dyes or pigments include, for example, methylene blue, crystal violet, Rhodamine B, fuchsin, aurin, azo dyes, anthraquinone dyes, titanium dioxide, carbon black, ferric oxide, phthalocyanine pigments, or azo pigments. Care has to be taken, however, that the absorption of the dye used is not too high in the initiation range of the photoinitiator.

Examples of plasticizers include phthalic acid esters, glycol esters, phosphoric acid esters, or aliphatic dicarboxylic acid esters.

The composition can also contain a sensitizer and/or an additional photoinitiator, selected to increase the photopolymerization rate, when they are used together with the photoinitiator of general formula I. Sensitizers that can be used include benzoin, benzoin alkylether, 9-fluorenone, 2-bromo-9-anthrone, 2-ethyl-9-anthrone, 9,10-anthraquinone, substituted anthraquinones, xanthone, substituted xanthones, thioxanthone, benzil, dibenzalacetone, substituted chalcones, benzophenone or benzanthrone, eosin or fluorescein derivatives, acridines, pyronines or similar substances.

Suitable co-initiators are, in particular, photoinitiators containing trichloromethyl groups, whose absorption peaks are clearly above the absorption peaks of the photoinitiators according to the present invention.

The 4,6-bis-trichloromethyl-s-triazin-2-yl-benzoylmethylene heterocycles described in the simultaneously-filed application Ser. No. 07/317,562 (corresponding to German No. P 38 07 381.1), are, for example, particularly suitable. By means of these measures the spectral sensitivity of the photosensitive composition can be extended over a large wavelength region.

The photopolymerizable composition can be used for various applications, for example, for the production of safety glass, as surface coatings that are cured by light or corpuscular radiation, for example electron beams, in the dental field and especially as a photosensitive copying material in the reproduction field. Possible applications of the latter include copying layers for the photomechanical production of printing forms for letterpress printing, flexographic printing, planographic printing, gravure printing and screen printing or relief copies, for example, for the preparation of texts in Braille, of single copies, tanned images, pigment images and the like. Moreover, the compositions can be used for the photomechanical production of etch resists, for example, for making name tags, printed circuits and for chemical milling.

The commercial use of the composition for the applications mentioned can take place in the form of a liquid solution or dispersion, for example, as a photoresist solution, applied by the user to an individual support, for example, for chemical milling and for the production of printed circuits, screen-printing stencils and the like. The composition can also be present as a solid photosensitive layer on a suitable support in the form of a precoated storable photosensitive copying material, for example, for the preparation of printing forms. It is likewise suitable for the preparation of dry resists.

In general, it is advantageous to protect the compositions from the influence of atmospheric oxygen during the photopolymerization. When the composition is used in the form of thin copying layers, it is advisable to apply a suitable covering film having low oxygen permeability. This film can be self-supporting and can be peeled off before the copying layer is developed. For example, polyester films are suitable for this purpose. The covering film can also comprise a material soluble in the developer fluid or can at least be removable from the unhardened areas during developing. Examples of materials suitable for this purpose are waxes, polyamides, polyvinyl alcohol, polyphosphates, sugars and the like.

Examples of suitable supports for copying materials produced with the composition according to the present invention are aluminum, steel, zinc, copper and plastic films, for example, of polyethylene terephthalate or cellulose acetate, and screen-printing supports such as gauze polyamide 6.

Moreover, the compounds according to the invention can be used in those radiation-sensitive compositions in which a change in properties is initiated by acid catalysts formed during the photolysis of the initiator. For instance, the cationic polymerization of systems containing vinyl ethers, N-vinyl compounds, such as N-vinylcarbazole, or special acid-cleavable lactones, may be mentioned here, whereby free-radical processes can also participate in some of these reactions. Further acid-curable compositions include aminoplasts, such as urea/formaldehyde resins, melamine/formaldehyde resins and other N-methylol compounds as well as phenol/formaldehyde resins. Even though the hardening of epoxy resins generally takes place by means of Lewis acids or acids, the anions of which are less nucleophilic than chloride (that is to say the anion of the hydrohalic acid that is formed during photolysis of the novel compounds) layers comprising epoxy resins and novolaks are, nevertheless, fully cured on exposure to light in the presence of compounds according to the invention.

A further advantageous property of the novel compounds is their ability to cause color changes in dyed systems during photolysis, namely to induce color formation from color precursors, for example, leuco compounds, or to effect bathochromic color shifts and deepening in compositions which contain cyanine, merocyanine or styryl dye bases. Moreover, for example, in the compositions described in DE-A 15 72 080, containing a dye base, N-vinylcarbazole and a halohydrocarbon, the halogen compound tetrabromomethane can be replaced by a compound according to the present invention in a quantity that is a fraction of the quantity of the former. Color changes are also desired in industry, for example, in the production of printing forms, so that the result of copying can be assessed after exposure even before developing.

The present compounds can be used advantageously in place of the acid donors mentioned in DE-A 23 31 377 and 26 41 100.

A particularly preferred field of application for the compounds according to the invention is in compositions that, in addition to the latter, contain a compound with at least one C—O—C grouping, that can be split by acid, as an essential component. The following are preferred compounds that can be split by acid:

A) those having at least one orthocarboxylate and/or carboxamide acetal grouping, it also being possible for the compounds to have a polymeric character and for the groupings to be present as linking elements in the main chain or as lateral substituents,
B) polymer or oligomer compounds with recurring acetal and/or ketal groupings or monomer acetals or ketals,
C) polymer compounds with recurring units of activated esters of carbonic acid.
D) compounds containing at least one enol ether or N-acyliminocarbonate group,
E) cyclic acetals or ketals of $\beta$-ketoesters or -amides,
F) compounds containing silyl ether groups,
G) compounds containing silylenol ether groups,
H) monoacetals or monoketals whose aldehyde or ketone components have a solubility in the developer between 0.1 and 100 g/l,
I) ethers based on the tertiary alcohols, and
K) carboxylates and carbonates of tertiary, allylic or benzylic alcohols.

Type A compounds, that can be split by acid, as components of radiation-sensitive compositions are described in detail in DE-A 26 10 842 and 29 28 636; compositions containing Type B compounds are the subject of DE-C 27 18 254, and compositions containing Type C compounds are described in EP-A 102 450.

As compounds that can be split by acid, the aryl alkyl acetals and aminals of DE-C 23 06 248, that are likewise degraded by the photolysis products of the compounds according to the present invention, may also be mentioned as examples.

Compounds of Type D are mentioned in EP-A 0 006 626 and 0 006 627; compounds of Type E are presented in EP-A 0 202 196; compounds belonging to F are presented in DE-A 35 44 165 and DE-A 36 01 264; compounds of Type G are found in U.S. patent application Ser. No. 243,819, filed Sept 13, 1988 and compounds of Type G are discussed in U.S. patent applications Ser. Nos. 243,818 and 243,792 likewise filed Sep. 13, 1988. Compounds of Type H are described, for example, in U.S. Pat. No. 4,603,101, and compounds of Type I for example, in U.S. Pat. No. 4,491,628 and by J. M.

Fréchet et al., *J. Imaging Sci.*, 30: 59-64 (1986). The contents of these references are hereby incorporated by reference.

Those compositions in which molecules are converted into smaller molecules directly or indirectly by the action of actinic radiation have, in general, an increased solubility, tackiness or volatility in the irradiated areas. These portions can be removed by suitable measures, for example, by dissolution with a developer fluid. In copying materials these are called positive-working systems.

The novolak condensation resins, proven in many positive copying materials, have also proved to be particularly useful and advantageous as additives when the compounds according to the invention are used in compositions with compounds that can be split by acid. The resins promote strong differentiation between exposed and unexposed layer portions on developing, in particular, the more highly condensed resins with substituted phenols as the formaldehyde condensation partners. The nature and quantity of the novolak resins can vary depending on the intended purpose. Amounts of novolak between about 30% and 90% by weight, particularly between about 55% and 85% by weight, based on total solids, are preferred.

In addition, numerous other resins can also be included, preferably vinyl polymers, such as polyvinyl acetates, polyacrylates, polyvinyl ethers and polyvinylpyrrolidones, which in turn can have been modified by comonomers. The most advantageous proportion of these resins depends on the requirements in the particular application and the influence on the developing conditions. In general, the proportion is not more than about 20% of the novolak. For special requirements, such as flexibility, adhesion and gloss and the like, the photosensitive composition can also contain small quantities of substances such as polyglycols, cellulose derivatives such as ethyl cellulose, wetting agents, dyes and finely-divided pigments as well as ultraviolet absorbers, when required. Developing is preferably carried out with the aqueous-alkaline developers common in industry that may contain small amounts of organic solvents, or with organic solvents.

The supports already listed in connection with the photopolymerizable compositions can also be used for positive-working copying materials. Further suitable supports are the silicon, silicon dioxide and gallium arsenide surfaces conventional in microelectronics.

The quantity of the compounds according to the invention, used as the acid donor, in positive-working compositions can vary widely depending on the substance and layer. Fairly advantageous results are obtained with quantities between about 0.1% and 10%, preferably between about 0.2% to 5%, based on total solids. For layers having thicknesses exceeding 10 μm it is advisable to use relatively small quantities of acid donor.

Electromagnetic radiation of wavelengths up to about 700 nm is in principle suitable for exposure. The preferred wavelength range extends from about 300 to 500 nm. The compositions of the present invention exhibit maximum sensitivity in the range between 350 and 400 nm.

The wide variety of the compounds according to the invention, the absorption peaks of which are often to be found at the envisaged wavelength of 365 nm, makes it possible to match the photoinitiator in an optimum manner to the light source used. Light sources include fluorescent tubes, pulsed xenon lamps, metal halide-doped mercury vapor high-pressure lamps and carbon arc lamps.

Moreover, with the photosensitive compositions according to the present invention, exposure in conventional projection and enlargement apparatus under the light of metal filament lamps and contact exposure with ordinary incandescent bulbs can advantageously be carried out. The exposure can also be made with the coherent light of a laser. Lasers that are suitable for the purposes of the present invention include, for example, argon ion lasers, krypton ion lasers, xenon ion lasers, dye lasers, helium/cadmium lasers or helium/neon lasers. The laser beam is, in general, monitored by means of a predetermined programmed line and/or screen movement.

Irradiation with electron beams is a further possibility. Electron beams can thoroughly decompose and crosslink compositions comprising one of the compounds according to the invention and a compound that can be split by acid, and also many other organic materials, so that a negative image is produced when the non-irradiated portions are removed by solvents or exposure without an original, and developing.

At a lower intensity and/or a higher writing speed of the electron beam, however, the electron beam effects a differentiation in the direction of higher solubility, that is to say the irradiated layer portions can be removed by the developer. The most advantageous conditions can readily be established by preliminary experiments.

The radiation-sensitive compositions comprising compounds according to the invention are preferably used in the production of positive-working or negative-working printing forms, in particular offset printing forms, letterpress printing forms, flexographic printing forms, halftone gravure printing forms and screen-printing forms, and in photoresist solutions and dry resists.

Owing to the properties of compounds according to the present invention photosensitive recording materials are obtained having numerous advantages compared with the prior art. Among these advantages, the high photosensitivity to light sources emitting light in the near ultraviolet region has to be especially mentioned. As a result, speedy exposure in accordance with practical requirements is insured using low-energy lasers emitting in the near ultraviolet region. The high susceptibility to atmospheric oxygen frequently observed in photosensitive compositions occurs to a minor degree, when the photoinitiators according to the present invention are employed. In addition, the photosensitive layers have an exceptionally high storage stability resulting from the high chemical and thermal stability of the photoinitiators of the invention. This means that stocks can be maintained and the solutions or photosensitive layers can be stored for a prolonged period of time. It is another important advantage that the photosensitive compositions, in which the photoinitiators or acid donors, respectively, of the present invention are used, undergo hardly any catalytically-initiated dark reactions on critical surfaces, e.g., copper surfaces. This alone represents an improvement over the prior art. Due to their slight inherent coloration the compounds of the invention can be used according to practical requirements, even in thick layers.

Although the photosensitive compositions are also sensitive to visible light and must therefore be handled under appropriate conditions, for example, under yellow light, the compounds of the present invention are extraordinarily stable to light and heat when in the crystalline state. They can therefore be prepared and handled without any greater expense under virtually normal production conditions and are stable for a long time in this state. Thus, stocks of these compounds can be maintained which are appropriate for practical purposes.

The examples that follow serve to explain the invention in more detail; the preparation of various compounds according to the invention is described first, and this is followed by the use of some of these compounds in radiation-sensitive compositions.

In the examples, parts by weight (pbw) and parts by volume (pbv) have the same relationship as the g and the ml. Unless otherwise stated, percentage data and quantitative data are to be understood as weight units.

PREPARATION EXAMPLE 1 a) 5-phenyltetrazole

Benzonitrile (11.5 pbw), lithium chloride (9.2 pbw) and sodium azide (15.7 pbw) are suspended in 400 pbv of 2-methoxy-ethanol and the mixture is heated to reflux for 15 hours. After cooling, the mixture is poured into 1000 pbv of water and stirred for 30 minutes. The insoluble constituents are removed by filtration and concentrated hydrochloric acid is then carefully added, until the mixture has been adjusted to a pH of 2. The mixture is cooled to 0° C. in an ice/sodium chloride cooling bath and is left standing overnight at this temperature. The precipitate is removed by filtration with suction and dried over phosphorus pentoxide.

Yield: 8 pbw of 5-phenyltetrazole.

b) methyl 4-(4,6-bis-trichloromethyl-s-triazin-2-yl) benzoate

Step 1: Pyridine (16 pbw) is added to hydroxylamine hydrochloride (14 pbw), and the mixture is stirred. 4-Methoxycarbonylbenzaldehyde (32.8 pbw) are added with stirring, causing the mixture to warm up. After 10 minutes, 200 pbw of m-xylene are added, and the mixture is heated to reflux in a water separator. After about 10 hours, the theoretical amount of water has separated. The mixture is allowed to cool to room temperature, is diluted with 200 pbw of diethyl ether and washed twice with 150 pbw each of distilled water. The organic phase is dried over magnesium sulfate, and the solvents are removed on a rotary evaporator, the last traces of xylene being evaporated under reduced pressure. The crude product obtained, mainly composed of methyl 4-cyanobenzoate, is recrystallized from 150 pbw of ethanol.

Step 2: The above-described dried product (16 pbw) is stirred with trichloroacetonitrile (86.6 pbw) and aluminum bromide (3.2 pbw) in the absence of moisture. The temperature of the clear solution is kept constant at 24° to 28° C., and hydrogen chloride gas is then passed into the solution with stirring until no more HCl absorption takes place (about 2 to 5 hours). The reaction product solidifies more and more during this time. Stirring is discontinued, and the syrup-like mixture is allowed to further react at room temperature for 24 hours. The yellow, solid reaction product is taken up in 500 pbw of dichloromethane and washed twice with 250 pbw each of distilled water. The organic phase is dried over sodium sulfate. After evaporation of the solvent, the white residue is recrystallized from 250 pbw of ethanol.

Yield: 41 pbw=91% of theory of white crystals of methyl 4-(4,6-bis-trichloromethyl-s-triazin-2-yl)benzoate.

MP: 157° to 158° C.

$C_{13}H_7N_3Cl_6O_2$ (449.9). calc.: C 34.70% H 1.51% N 9.34% Cl 47.28%. found: C 34.6% H 1.4% N 9.1% Cl 47.7%.

c) 4-(4,6-bis-trichloromethyl-s-triazin-2-yl)benzoic acid

Methyl 4-(4,6-bis-trichloromethyl-s-triazin-2-yl)benzoate (125 pbw), trichloroacetic acid (250 pbw) and concentrated sulfuric acid (2 pbw) are heated to 175° C. with stirring. At this temperature, the methyl trichloroacetate formed is removed by distillation. After about 40 pbw of methyl trichloroacetate have been distilled, a slight vacuum of 270 mbar is established to complete the distillation. The residue is allowed to cool to 80° C. and then added to 1500 pbw of ice water. The mixture is triturated for 30 minutes, and the product is then removed by filtration with suction.

Yield: 87 pbw =72% of theory, white crystals (from toluene) of MP 275° C.

$C_{12}H_5N_3O_2Cl_6$ (435.9). calc.: C 33.06% H 1.16% N 9.64% Cl 48.80% found: C 33.3% H 1.0% N 9.6% Cl 48.3% d) 4-(4,6-bis-trichloromethyl-s-triazin-2-yl)benzoyl chloride 4-(4,6-Bis-trichloromethyl-s-triazin-2-yl)benzoic acid (87 pbw) is added to thionyl chloride (350 pbw). Upon heating to reflux in the absence of moisture and with vigorous stirring, a distinct evolution of $SO_2$ can be observed. After 6 hours, a clear solution is present. Excess thionyl chloride is removed by distillation, towards the end by applying a vacuum.

The residue contains in virtually quantitative yield pure 4-(4,6-bis-trichloromethyl-s-triazin-2-yl)benzoyl chloride and is recrystallized from hexane, MP 100° to 101° C.

$C_{12}H_4N_3OCl_7$ (454.3). calc.: C 31.72% H 0.89% N 9.25% Cl 54.62%. found: C 31.9% H 0.7% N 9.3% Cl 54.7%.

e) 2-[4-(4,6-bis-trichloromethyl-s-triazin-2-yl)phenyl]-5-phenyl-1,3,4-oxadiazole (Compound No. 1)

5-Phenyltetrazole (5 pbw) and 4-(4,6-bis-trichloromethyl-s-triazin-2-yl)benzoyl chloride (15.5 pbw) are dissolved in 125 pbv of pyridine and slowly heated to reflux. At about 80° C. nitrogen evolution commences, which comes to an end after about 1 hour. After cooling, the mixture is poured into 500 pbv of ice water, the precipitate that deposits is removed by filtration and is, after drying, recrystallized from 2-methoxyethanol.

Yield: 15.2 pbw=83.5% of theory, flesh-colored crystals, MP 226 to 227.5° C.

$C_{19}H_9Cl_6N_5O$ (536.0). calc.: C 42.57% H 1.69% N 13.06% Cl 39.68% found: C 42.3% H 1.6% N 12.8% Cl 40.1%; UV ($CH_2Cl_2$): λ max=330 nm.

PREPARATION EXAMPLE 2 a) 5-(3,4-dimethoxyphenyl)-tetrazole 3,4-Dimethoxy benzonitrile (18.1 pbw), lithium chloride (9.1 pbw) and sodium azide (15.7 pbw) are heated to reflux for 16 hours in 400 pbv of 2-methoxy-ethanol. After cooling, about two thirds of the solvent are distilled off and the remaining mixture is poured into 1000 pbv of water. The clear solution obtained is cooled to 0° C., acidified and the precipitate that deposits is removed by filtration, washed with water and dried.

Yield: 13.5 pbw of 5-(3,4-dimethoxyphenyl)tetrazole.

b)
2-[4-(4,6-bis-trichloromethyl-s-triazin-2-yl)phenyl]-5-(3,4-dimethoxyphenyl)-1,3-4-oxadiazole (Compound No. 7)

5-(3,4-Dimethoxyphenyl)-tetrazole (20 pbw) and 4-(4,6-bis-trichloromethyl-s-triazin-2-yl)benzoyl chloride (44 pbw) are slowly heated to reflux in 200 pbv of pyridine, with a strong evolution of nitrogen occurring in the process. After 1.5 hours, the solution is cooled, poured into 1000 pbv of water and after complete precipitation, the product is removed by filtration with suction. After drying, the product is recrystallized from 2-methoxy-ethanol.

Yield: 36 pbw=62.9% of theory, yellowish crystals, MP 214° to 215° C.

$C_{21}H_{13}Cl_6N_5O_3$ (596.1). calc.: C 42.31% H 2.20% N 11.75% Cl 35.69%. found: C 42.1% H 2.2% N 11.7% Cl 36.2%.

UV (CH$_2$Cl$_2$): λ max=353 nm.

PREPARATION EXAMPLE 3 a) 3-(4,6-bis-trichloromethyl-s-triazin-2-yl)benzoyl chloride

Thionyl chloride (240 pbw) and toluene (240 pbw) are mixed, and 140 pbw of 3-cyanobenzoic acid are added. The suspension is stirred in the absence of moisture and heated to reflux. After about 5 hours, the evolution of SO$_2$ is complete, and the solution is clear. Excess thionyl chloride and toluene are removed by distillation, and the residue is poured carefully into 600 pbw of methanol. The mixture is left to stand for 24 hours and then cooled to 0° C. to complete the precipitation. The precipitate of methyl 3-cyanobenzoate is removed by filtration with suction and dried over phosphorus pentoxide. The above-described compound is reacted with trichloroacetonitrile to form the methyl 3-(4,6-bis-trichloromethyl-s-triazin-2yl)benzoate (MP 115° to 117° C.), as described in Preparation Example 1. By reacting this compound with trichloroacetic acid, as in Preparation Example 1, the corresponding benzoic acid (MP 211.5° C.) is prepared and by reacting the latter with thionyl chloride the acid chloride (MP 102° to 103° C.) is obtained.

b)
2-[3-(4,6-bis-trichloromethyl-s-triazin-2-yl)phenyl]-5-(3,4-dimethoxyphenyl)-1,3,4-oxadiazole (Compound No. 23)

5-(3,4-Dimethoxyphenyl)-tetrazole (20 pbw) and 3-(4,6-bis-trichloromethyl-s-triazin-2-yl)benzoyl chloride (44 pbw) are heated in 400 pbv of pyridine. The mixture is further processed as indicated above.

Yield: 52 pbw=90.8% of theory, virtually colorless crystals, MP 195° to 196° C.

$C_{21}H_{13}Cl_6N_5O_3$ (596.1). calc.: C 42.31% H 2.20% N 11.75% Cl 35.69%. found: C 42.2% H 2.2% N 11.7% Cl 36.9%.

UV (CH$_2$Cl$_2$): λ max=306 nm.

PREPARATION EXAMPLE 4 a) methyl 4-(4,6-bis-trichloromethyl-s-triazin-2-yl) cinnamate

Step 1: 4-Cyanocinnamic acid (50 pbw), absolute methanol (27.7 pbw), 1,2-dichloroethane (200 pbw) and toluenesulfonic acid (1.6 pbw) are heated to reflux for about 15 hours. Monitoring at this point by thin-layer chromatography shows that the reaction has gone to completion. The clear solution is cooled with ice, after which some of the product crystallizes and is isolated by filtration. The mother liquor is washed with 5% strength sodium bicarbonate solution and washed twice with water. After drying of the organic phase over magnesium sulfate, the solvent is evaporated and the resulting product is dried over phosphorus pentoxide. The two batches of methyl 4-cyanocinnamate are combined, since both have the same purity.

The ester obtained is used to prepare the methyl 4-(4,6-bis-trichloromethyl-s-triazin-2-yl) cinnamate analogously to Preparation Example 1(b).

b) 4-(4,6-bis-trichloromethyl-s-triazin-2-yl) cinnamic acid

In a flask flushed with dry nitrogen are placed 450 pbw of dry 1,2-dichloroethane, 49.2 pbw of hexamethyldisilane and 85.3 pbw of iodine. Methyl 4-(4,6-bis-trichloromethyl-s-triazin-2-yl) cinnamate (80 pbw) are added in portions, during which the reaction which sometimes proceeds exothermically and is kept under control by cooling. After the addition is complete, the mixture is heated to reflux using a cooling system operating at −20° C., which is continued until thin-layer chromatography indicates a virtually complete conversion (4 to 12 hours). Atter cooling, 400 pbw of water are added to the reaction mixture, which is concentrated on a rotary evaporator until the dichloroethane has been evaporated. Methanol is added to the remaining aqueous mixture, precipitating the acid quantitatively. This acid is removed by filtration with suction and recrystallized from glacial acetic acid (the recrystallized product then contains 1 molecule of glacial acetic acid) or a water/glacial acetic acid mixture.

Yield: 60.5 pbw=78% of theory, MP 233° to 234° C. $C_{14}H_7N_3O_2Cl_6$ (461.9). calc.: C 36.40% H 1.53% N 9.10% Cl 46.05%. found: C 36.2% H 1.35% N 8.9% Cl 46.5%.

The compound obtained is used to prepare the 4-(4,6-bis-trichloromethyl-s-triazin-2-yl) cinnamoyl chloride (MP 156° to 158° C.) analogously to Preparation Example 1(d).

c)
2-[4-(4,6-bis-trichloromethyl-s-triazin-2-yl)phenylethenyl]-5-(3,4-dimethoxyphenyl)-1,3,4-oxadiazole (Compound No. 37)

5-(3,4-Dimethoxyphenyl)-tetrazole (20 pbw) is heated to reflux with 4-(4,6-bis-tri-chloromethyl-s-triazin-2-yl)-cinnamic acid chloride (48 pbw) in 400 pbv of pyridine. After a reaction time of about 1 hour, the dark mixture is cooled and poured into water. By slowly adding hydrochloric acid, the pH of the mixture is adjusted to 3 to 4 and the mixture is then extracted by shaking with a 1:1 mixture of ether and tetrahydrofuran. The organic phase is washed with water, dilute sodium bicarbonate solution and again with water and is dried over calcium chloride. The solvents are evaporated and the residue is triturated in toluene. The constituents that have not dissolved are removed by filtration.

Yield: 30 pbw = 52.4% of theory, yellow crystals, MP 241.5° to 242° C. (decomposition).

$C_{23}H_{15}Cl_6N_5O_3$ (622.1). calc.: C 44.40% H 2.43% N 11.26% Cl 34.19%. found: C 44.7% H 2.5% N 11.1% Cl 34.4%.

UV ($CH_2Cl_2$): $\mu$ max = 369 nm.

PREPARATION EXAMPLE 5 a) 5-(3,4-dimethoxy-phenylethenyl)-tetrazole 3,4-Dimethoxy cinnamic acid nitrile (9.8 pbw), lithium chloride (4.3 pbw) and sodium azide (7.4 pbw) are heated to reflux for 16 hours in 200 pbv of 2-methoxy-ethanol. After cooling, the mixture is poured into 4000 pbv of water. The clear solution obtained is cooled to 0° C., acidified and the precipitate that deposits is removed by filtration, washed with water and dried.

Yield: 9 pbw of 5-(3,4-dimethoxyphenylethenyl)-tetrazole.

b) 2-[4-(4,6-bis-trichloromethyl-s-triazin-2-yl)phenyl]-5-(3,4-dimethoxy-phenylethenyl)-1,3,4-oxadiazole (Compound No. 30)

The compound described under (a) above (20 pbw) and 4-(4,6-bis-trichloromethyl-s-triazin-2-yl)-cinnamic acid chloride (40 pbw) are slowly heated to reflux in 200 pbv of pyridine, with a strong nitrogen evolution occurring in the process. After 1.5 hours, the solution is cooled and poured into 500 pbv of water and after complete precipitation the product is removed by filtration with suction. After drying, the product is recrystallized from 2-methoxy-ethanol.

Yield: 28 pbw = 52.4% of theory, yellowish crystals, MP 207° to 208° C.

$C_{23}H_{15}Cl_6N_5O_3$ (622.1). calc.: C 44.40% H 2.43% N 11.26% Cl 34.19%. found: C 44.4% H 2.4% N 11.2% Cl 34.4%.

UV ($CH_2Cl_2$): $\lambda$ max = 373 nm.

PREPARATION EXAMPLE 6 a) 5-(1-naphthyl)-tetrazole

1-Naphthonitrile (40 pbw), lithium chloride (21.5 pbw) and sodium azide (34.7 pbw) are heated to reflux for 16 hours in 750 pbv of 2-methoxy-ethanol. After cooling, the mixture is poured into 4000 pbv of water. The mixture obtained is filtered, cooled to 0° C. and the precipitate that deposits after acidifying is removed by filtration, washed with water and dried.

Yield: 29 pbw of 5-(1-naphthyl)-tetrazole.

b) 2-4-(4,6-bis-trichloromethyl-s-triazin-2-yl)phenyl]-5-(1-naphthyl)-1,3,4-oxadiazole (Compound No. 16)

The compound described under (a) above (26.7 pbw) and 4-(4,6-bis-trichloromethyl-s-triazin-2-yl)-benzoyl chloride (93 pbw) are slowly heated to reflux in 300 pbv of pyridine, with a strong nitrogen evolution occurring in the process. After 1.5 hours, the solution is cooled and poured into 800 pbv of water and after complete precipitation the product is removed by filtration with suction. After drying, the product is recrystallized from 2-methoxyethanol.

Yield: 57 pbw = 71.5% of theory, yellowish crystals, MP 298° C.

$C_{23}H_{11}Cl_6N_5O$ (586.1). calc.: C 47.13% H 1.89% N 11.95% Cl 36.29%. found: C 47.1% H 1.9% N 11.7% Cl 36.0%.

UV ($CH_2Cl_2$): $\lambda$ max = 348 nm.

PREPARATION EXAMPLE 7 a) 5-(2-naphthyl)-tetrazole 2-naphthonitrile (40 pbw), lithium chloride (21.5 pbw) and sodium azide (34.7 pbw) are heated to reflux for 16 hours in 750 pbv of 2-methoxyethanol. After cooling, the mixture is poured into 4000 pbv of water. The mixture obtained is filtered, cooled to 0° C. and acidified. The precipitate that deposits is removed by filtration, washed with water and dried.

Yield: 46 pbw of 5-(2-naphthyl)tetrazole.

b) 2-[4-(4,6-bis-trichloromethyl-s-triazin-2-yl)phenyl]-5-(2-naphthyl)-1,3,4-oxadiazole (Compound No. 17)

The compound described under (a) above (19.6 pbw) and 4-(4,6-bis-trichloromethyl-s-triazin-2-yl)-benzoyl chloride (45.4 pbw) are slowly heated to reflux in 300 pbv of pyridine, with a strong nitrogen evolution occurring in the process. After 1.5 hours, the solution is cooled and poured into 800 pbv of water and after complete precipitation the product is removed by filtration with suction. After drying, the product is recrystallized from ethanol.

Yield: 46 pbw = 77.8% of theory, faintly yellowish crystals, MP 248° to 250° C.

$C_{23}H_{11}Cl_6N_5O$ (586.1). calc.: C 47.13% H 1.89% N 11.95% Cl 36.29%. found: C 46.8% H 1.7% N 11.6% Cl 36.6%.

UV ($CH_2Cl_{12}$): $\lambda$ max = 336 nm.

PREPARATION EXAMPLE 8 a) 5-(4-diphenylaminophenyl)-tetrazole

4-Diphenylaminobenzonitrile (81 pbw), lithium chloride (47 pbw) and sodium azide (72 pbw) are heated to reflux for 96 hours in 1050 pbv of 2-methoxy-ethanol. After cooling, the mixture is poured into 3000 pbv of water. Active charcoal is added to the mixture obtained, which is then filtered, cooled to 0° C. and acidified to pH = 5. The precipitate that deposits is removed by filtration, washed with water and dried.

Yield: 84 pbw of 5-(4-diphenylaminophenyl)tetrazole.

b) 2-[3-(4,6-bis-trichloromethyl-s-triazin-2-yl) phenyl]-5-(4-diphenylaminophenyl)-1,3,4-oxadiazole (Compound No. 26)

The compound described under (a) above (31.4 pbw) and 3-(4,6-bis-trichloromethyl-s-triazin-2-yl)-benzoyl chloride (45.4 pbw) are slowly heated to reflux in 300 pbv of pyridine, with a strong nitrogen evolution occurring in the process. After 1.5 hours, the solution is cooled and poured into 800 pbv of water and after complete precipitation the product is removed by filtration with suction. After drying, the product is recrystallized from ethanol/toluene.

Yield: 52 pbw 73.9% of theory, yellow crystals, MP 238° to 239° C.

$C_{31}H_{18}Cl_6N_6O$ (703.2). calc.: C 52.96% H 2.58% N 11.95% Cl 30.25%. found: C 52.5% H 2.8% N 11.6% Cl 30.3%.

UV ($CH_2Cl_2$): $\lambda$ max = 360 nm.

PREPARATION EXAMPLE 9

2-[4-(4,6-bis-trichloromethyl-s-triazin-2-yl)phenyl]-5-(4-diphenylaminophenyl)-1,3,4-oxadiazole (Compound No. 18)

The compound described under (a) in Preparation Example 8 (31.4 pbw) and 4-(4,6-bis-trichloromethyl-s-triazin-2-yl)-benzoyl chloride (45.4 pbw) are slowly heated to reflux in 300 pbv of pyridine, with a strong nitrogen evolution occurring in the process. After 1.5 hours, the solution is cooled and poured into 800 pbv of water and after complete precipitation the product is removed by filtration with suction. After drying, the product is recrystallized from ethanol/chloroform.

Yield: 46 pbw=65.4% of theory, yellow crystals, MP 209° to 210.5° C.

$C_{31}H_{18}Cl_6N_6O$ (703.2). calc.: C 52.95% H 2.58% N 11.95% Cl 30.25%. found: C 53.1% H 2.4% N 11.5% Cl 29.4%.

UV ($CH_2Cl_2$): λ max=403 nm.

PREPARATION EXAMPLE 10 a) 5-(4-chlorophenyl)-tetrazole 4-chlorobenzonitrile (15.3 pbw), lithium chloride (9.1 pbw) and sodium azide (15.7 pbw) are heated to reflux for 24 hours in 450 pbv of 2-methoxy-ethanol. After cooling, the mixture is poured into 1000 pbv of water. The mixture obtained is filtered, cooled to 0° C. and acidified to pH=3. The precipitate that deposits is removed by filtration, washed with water and dried.

Yield: 18 pbw of 5-(4-chlorophenyl)tetrazole.

b) 2-[4-(4,6-bis-trichloromethyl-s-triazin-2-yl)phenyl]-5-(4-chlorophenyl)-1,3,4-oxadiazole (Compound No. 9)

The compound described under (a) above (24.6 pbw) and 4-(4,6-bis-trichloromethyl-s-triazin-2-yl)-benzoyl chloride (93 pbw) are slowly heated to reflux in 300 pbv of pyridine, with a strong nitrogen evolution occurring in the process. A clear solution does not form at any time in the reaction process. After 1.5 hours, the solution is cooled and poured into 800 pbv of water and after complete precipitation the product is removed by filtration with suction. After drying, the product is recrystallized from 2-methoxyethanol.

Yield: 70 pbw 90.2% of theory, flesh-colored, slightly yellow crystals, MP 273° C.

$C_{19}H_8Cl_7N_5O$ (570.5). calc.: C 40.00% H 1.41% N 12.28% Cl 43.50%. found: C 39.8% H 1.4% N 12.1% Cl 43.4%.

UV ($CH_2Cl_2$): λ max=332 nm.

PREPARATION EXAMPLE 11

Step (a) of Preparation Example 1 is modified in such a way that an equivalent amount of ammonium chloride is substituted for the lithium chloride and dimethyl formamide is used instead of 2-methoxy-ethanol. The mixture is heated at 110° C. for 16 hours, relatively large crystals of ammonium azide crystallizing in the condenser. The mixture is further processed as indicated in Preparation Example 1.

The yield obtained comprises 9 pbw of 5-phenyltetrazole.

The further reaction is carried out as specified in Preparation Example 1; the product obtained has a melting point of 227° C..

PREPARATION EXAMPLE 12

Step (a) of Preparation Example 1 is modified in such a way that an equivalent amount of ammonium chloride is substituted for the lithium chloride. The mixture is heated to reflux for 16 hours, ammonium azide crystallizing in the condenser. The mixture is further processed as indicated in Preparation Example 1. The yield obtained comprises 5 pbw of 5-phenyltetrazole. The following Table lists all compounds of formula I, which have been prepared and examined.

TABLE I

Compounds of formula I

| Compound No. | $R^1$ | n | m | $R^2$ | $R^3$ |
|---|---|---|---|---|---|
| 1 | phenyl | 0 | 0 | H | X |
| 2 | 4-tolyl | 0 | 0 | H | X |
| 3 | 3-tolyl | 0 | 0 | H | X |
| 4 | 4-methoxyphenyl | 0 | 0 | H | X |
| 5 | 3-methoxyphenyl | 0 | 0 | H | X |
| 6 | 2-methoxyphenyl | 0 | 0 | H | X |
| 7 | 3,4-dimethoxyphenyl | 0 | 0 | H | X |
| 8 | 3,4,5-trimethoxyphenyl | 0 | 0 | H | X |
| 9 | 4-chlorophenyl | 0 | 0 | H | X |
| 10 | 2,4-dichlorophenyl | 0 | 0 | H | X |
| 11 | 4-nitrophenyl | 0 | 0 | H | X |
| 12 | 4-cyanophenyl | 0 | 0 | H | X |
| 13 | 4-formylphenyl | 0 | 0 | H | X |
| 14 | 3-trifluoromethylphenyl | 0 | 0 | H | X |
| 15 | biphenyl-4-yl | 0 | 0 | H | X |
| 16 | 1-naphthyl | 0 | 0 | H | X |
| 17 | 2-napthyl | 0 | 0 | H | X |
| 18 | 4-diphenylaminophenyl | 0 | 0 | H | X |
| 19 | 3-pyridyl | 0 | 0 | H | X |
| 20 | N-ethyl-carbazol-3-yl | 0 | 0 | H | X |
| 21 | 4-tolyl | 0 | 0 | X | H |
| 22 | 4-methoxyphenyl | 0 | 0 | X | H |
| 23 | 3,4-dimethoxyphenyl | 0 | 0 | X | H |
| 24 | 4-chlorophenyl | 0 | 0 | X | H |
| 25 | biphenyl-4-yl | 0 | 0 | X | H |
| 26 | 4-diphenylaminophenyl | 0 | 0 | X | H |
| 27 | N-ethyl-carbazol-3-yl | 0 | 0 | X | H |
| 28 | phenyl | 1 | 0 | H | X |
| 29 | 4-methoxyphenyl | 1 | 0 | H | X |
| 30 | 3,4-dimethoxyphenyl | 1 | 0 | H | X |
| 31 | 3,4-methylendioxyphenyl | 1 | 0 | H | X |
| 32 | phenyl | 1 | 0 | X | H |
| 33 | 4-tolyl | 1 | 0 | X | H |
| 34 | 4-methoxyphenyl | 1 | 0 | X | H |
| 35 | 3,4-dimethoxyphenyl | 1 | 0 | X | H |
| 36 | 4-tolyl | 0 | 1 | H | X |
| 37 | 3,4-dimethoxyphenyl | 0 | 1 | H | X |
| 38 | 4-methoxyphenyl | 1 | 1 | H | X |
| 39 | 4-tolyl | 0 | 1 | X | H |
| 40 | biphenyl-4-yl | 0 | 1 | X | H |
| 41 | 4-tolyl | 1 | 1 | X | H |
| 42 | 4-methoxyphenyl | 1 | 1 | X | H |

X = 4,6-bis-trichloromethyl-s-triazin-2-yl

The compounds that have not been described in the Preparation Examples have absorption peaks at the wavelengths specified in the following Table II (solvent: $CH_2Cl_2$):

TABLE II

| No. | λmax (nm) | No. | λmax (nm) |
|---|---|---|---|
| 2 | 336 | 24 | 304 |
| 3 | 332 | 25 | 323 |
| 4 | 348 | 27 | 379 |
| 5 | 338 | 28 | 347 |
| 6 | 351 | 29 | 368 |
| 8 | 354 | 31 | 370 |
| 10 | 333 | 32 | 318 |
| 11 | 332 | 33 | 321 |
| 12 | 330 | 34 | 333 |
| 13 | 332 | 35 | 334 |
| 14 | 325 | 36 | 361 |
| 15 | 342 | 38 | 377 |

TABLE II-continued

| No. | λmax (nm) | No. | λmax (nm) |
|---|---|---|---|
| 19 | 335 | 39 | 320 |
| 20 | 426 | 40 | 323 |
| 21 | 304 | 41 | 339 |
| 22 | 310 | 42 | 351 |

APPLICATION EXAMPLE 1

An aluminum sheet electrochemically-grained and anodically-oxidized to produce an oxide layer of 2.5 g/m$^2$ is pretreated with an aqueous solution of polyvinyl phosphonic acid. The support material so prepared is coated with a solution of the following composition:
- 91.2 pbw of a 31% strength solution of a terpolymer of styrene, n-hexyl-methacrylate and methacrylic acid (10:60:30) having an acid number of 190, in butanone,
- 54.9 pbw of a 51.5% strength solution of the reaction product of 1 mole of hexamethylene diisocyanate and 2 moles of hydroxyethyl methacrylate,
- 2.8 pbw of compound No. 4, and 660 pbw of 2-methoxy-ethanol.

A dry-layer weight of 3.0 g/m$^2$ is obtained by spin-coating and drying for 2 minutes at 100° C. The photosensitive layer is coated with a covering layer of polyvinyl alcohol.

The printing plate obtained is exposed for 5 seconds to the light of a 5 kW metal halide lamp arranged at a distance of 110 cm, under a 13-step exposure wedge containing additional line and screen elements. After exposure the plate is heated for 1 minute at 100° C. The plate is then developed with a developer of the following composition:
- 60 pbw of sodium metasilicate×9 H$_2$O,
- 1.06 pbw of strontium chloride×6 H$_2$O,
- 0.6 pbw of a non-ionic wetting agent, and
- 2000 pbw of demineralized water.

The plate is crosslinked up to step 4. The fine line and screen elements are satisfactorily rendered. After clamping onto a sheet-fed offset-printing machine the plate readily accepts the ink supplied and produces a print run of over 100,000 prints.

APPLICATION EXAMPLE 2

A coating solution of the composition indicated below is prepared and applied to an aluminum sheet pretreated as described in Application Example 1, to give a dry-layer weight of 2.8 g/m$^2$:
- 102.6 pbw of a copolymer of methyl methacrylate and methacrylic acid (82:18) having an acid number of 118, added as a 34.4% strength solution in butanone,
- 36 pbw of trimethylolethane triacrylate,
- 0.7 pbw of a blue azo dye, obtained by coupling 2,4-dinitro-6-chloro-benzenediazonium salt with 2-methoxy-5-acetylamino-N-cyanoethyl-N-hydroxyethyl-aniline, and
- 1.56 pbw of compound No. 7 in
- 462 pbw of 2-methoxy-ethanol.

The photosensitive layer is coated with a covering layer of polyvinyl alcohol, exposed for 30 seconds as described in Application Example 1 and developed with the developer there specified, without an additional heating operation.

A high-resolution plate is obtained, yielding almost 200,000 prints when used on a sheet-fed offset-printing machine.

APPLICATION EXAMPLE 3

As described in Application Example 1, a photosensitive solution of the following composition is coated onto an aluminum sheet to give a dry layer weight of 3.0 g/m$^2$ and is coated with a covering layer:
- 32.83 pbw of a reaction product obtained by reacting a polyvinyl butyral containing 71% by weight of vinyl butyral units, 2% by weight of vinyl acetate units and 27% by weight of vinyl alcohol units with propenylsulfonyl isocyanate, having an acid number of 145 and being added as a 12% strength solution in tetrahydrofuran,
- 0.03 pbw of the blue azo dye indicated in Application Example 2,
- 3.94 pbw of the monomer described in Application Example 1, and
- 0.37 pbw of compound No. 16, in
- 87.42 pbw of 2-methoxy-ethanol.

The plate is exposed and developed as indicated in Application Example 1. In this case, a fully-crosslinked step 5 is obtained at an exposure time of 12 seconds; all screen and line elements are satisfactorily rendered. A print run of 160,000 is obtained.

APPLICATION EXAMPLE 4

A solution of:
- 66 pbw of the terpolymer described in Application Example 1,
- 42 pbw of polypropylene glycol-420-dimethacrylate,
- 0.2 pbw of the dye specified in Application Example 2,
- 2.5 pbw of compound No. 26, in
- 240 pbw of butanone, and
- 30 pbw of 2-methoxy-ethanol is spin-coated onto a phenoplast laminate clad with a 35 μm thick copper foil to give a layer thickness of 45 μm after drying at 100° C. The plate is exposed for 40 seconds to the light of a 5 kW metal halide lamp arranged at a distance of 110 cm from the vacuum frame. The originals used comprise a 13-step exposure wedge with density increments of 0.15 and also a line original with line widths and spaces down to 80 μm.

After exposure the layer is developed for 100 seconds with an 0.8% strength sodium carbonate solution in a spray developing apparatus. Five fully-crosslinked wedge steps are obtained.

The plate is then rinsed for 30 seconds with tap water, etched for 30 seconds in a 15% strength ammonium peroxydisulfate solution, again rinsed with water, immersed for 30 seconds into a 10% strength sulfuric acid and then electroplated successively in the following electrolyte baths:
1) 50 minutes in a copper electrolyte bath available from Schloetter, Geislingen/Steige
   Type: "Glanzkupferbad PC"
   Current density: 2.5 A/dm$^2$
   Metal deposit: approx. 25 μm
   Temperature: room temperature,
2) 15 minutes in a lead-tin bath LA available from Schloetter, Geislingen/Steige
   Current density: 2 A/dm$^2$
   Metal deposit: 15 μm
   Temperature: room temperature.

The plate does not exhibit any undercutting or damage. The overhang or the inclination, respectively, of a side wall of the resist layer is less than 10 μm for a resist width of 140 μm.

The resist stencil can be removed in a 5% strength KOH solution at 50° C. and the bared copper can then be etched away in the customary etching media.

APPLICATION EXAMPLE 5

A mechanically-grained aluminum sheet is spin-coated with a solution of
.75 pbw of a cresol/formaldehyde novolak having a melting range from 105° to 120° C.,
23.8 pbw of a polyacetal of triethylene glycol and 2-butyraldehyde,
0.02 pbw of crystal violet base, and
0.6 pbw of compound No. 36, in
24 pbw of 2-methoxy-ethanol, and
275 pbw of butanone and dried. The plate is exposed through an original containing a step wedge and fine line and screen elements. Development is carried out with a solution of:
5.5 pbw of sodium metasilicate×9 $H_2O$,
3.4 pbw of trisodium phosphate×12 $H_2O$, and
0.4 pbw of sodium dihydrogen phosphate in
90.7 pbw of demineralized water.

At an exposure time of 35 seconds and development after a delay of 10 minutes, 4 completely-developed wedge steps are obtained. The test elements are rendered down to the 10 μm range.

APPLICATION EXAMPLE 6

A positive dry-resist solution of the following composition is prepared:
21.2 pbw of the novolak described in Application Example 5,
10 pbw of the bis-(5-ethyl-5-butyl-1,3-dioxan-2-yl) ether of 2-ethyl-2-butyl-1,3-propanediol,
0.05 pbw of crystal violet base
3.8 pbw of polyethylacrylate of low viscosity, and
0.25 pbw of compound No. 42, in
65 pbw of butanone.

A biaxially-stretched and thermoset, 25 μm thick polyester film, pretreated with an aqueous trichloroacetic acid/polyvinyl alcohol solution, is coated with this solution. The dry layer weight is 45 g/m². This layer is laminated to both sides of a copper sheet and after cooling, peeling off the support film and post-baking in a drying cabinet at 80° C., the coated sheet is exposed on both sides with a congruent pair of originals in the form of a pocket. The exposed layer areas are developed by spray developing, using the developer solution described in Application Example 5. The plate is etched on both sides with a commercially-available ferric chloride solution until it was cleanly etched through. The resist stencils are removed with a 4% strength KOH solution and a chemically-milled component is obtained which is a perfect reproduction of the original.

APPLICATION EXAMPLE 7

In accordance with Application Example 1, five photosensitive printing plates are prepared and heated at 100° C. in a circulating-air oven for one, two, three and four hours, in the unexposed state. Upon termination of the respective heating times the plates are removed from the oven, cooled, exposed for 15 seconds and further processed as described in Application Example 1. For comparison, a plate not heated is exposed and processed in the same way.

The plates heated for one, two and three hours, respectively, are not practically different from the comparative sample, while the plate heated for four hours exhibits one additional crosslinked step of the continuous-tone step wedge.

This example shows the extraordinarily good thermal stability of the composition according to the present invention.

APPLICATION EXAMPLE 8

Aluminum sheets coated as described in Application Example are kept, in the unexposed state, in a hotbox at a temperature of 56° C., for two, six and thirteen weeks, respectively. After the plates are removed from the hotbox they are further processed as described in Application Example 1.

Even after three months, storage in the hotbox exposed and developed plates and also prints produced therefrom do not show any significant difference from the original plate of Application Example 1.

The plates thus have an excellent storage stability at an elevated temperature.

APPLICATION EXAMPLE 9

Aluminum sheets coated as described in Application Example 1 are kept, in the unexposed state, in a cabinet under tropical conditions, at a temperature of 42° C. and a relative humidity of 60%, for two, six and thirteen weeks, respectively. After the plates are removed from the cabinet they are further processed as described in Application Example 1.

Even after three months' storage under tropical conditions exposed and developed plates and also prints produced therefrom do not show any significant difference from the original plate of Application Example 1.

The plates thus have an excellent storage stability under tropical conditions.

APPLICATION EXAMPLE 10 AND COMPARATIVE EXAMPLE 11

A mechanically-grained aluminum sheet is spin-coated with a solution of:
75 pbw of the novolak specified in Application Example 5,
23.8 pbw of a polyacetal of triethylene glycol and 2-butyraldehyde,
0.02 pbw of crystal violet base, and
0.6 pbw of compound No. 29, in
24 pbw of 2-methoxy-ethanol, and
275 pbw of butanone and dried.

For comparison compound No. 29 in the above formulation is replaced by an equivalent amount of the compound 2-trichloromethyl-5-(4-methoxyphenylethenyl)-1,3,4-oxadiazole (compound No. 7 of DE-A 28 51 471) and a plate is prepared with the solution obtained, which is otherwise identical. In both cases a dry-layer weight of 2.2 g/m² results.

The plates are exposed through an original containing a step wedge and fine line and screen elements. Development is carried out with a solution of:
5.5 pbw of sodium metasilicate×9 $H_2O$,
3.4 pbw of trisodium phosphate×12 $H_2O$, and
0.4 pbw of sodium dihydrogen phosphate in
90.7 pbw of demineralized water.

At an exposure time of 50 seconds and development after a delay of 10 minutes, about 4 to 5 completely-developed wedge steps are obtained with compound No. 29. The test elements are rendered down to the 10 μm range. When the comparative compound is used, 2 to 3 completely-developed wedge steps are obtained, resolution of the test elements is effected down to about 15 to 20 μm.

What is claimed is:

1. A compound of formula I

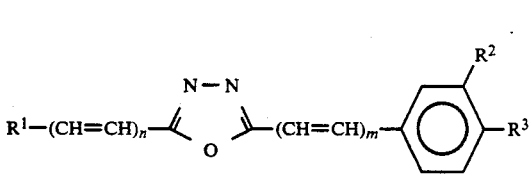

wherein
$R^1$ is one of a phenyl radical either unsubstituted or substituted by 1 to 3 alkyl, alkoxy, phenyl, perhaloalkyl, nitro, cyano, carboxyl, carbonyl or diphenylamino groups, a tolyl radical, a naphthyl radical, a biphenyl radical,
a carbazolyl radical and a pyridyl radical,
one of $R^2$ and $R^3$ is a hydrogen atom and the other of $R^2$ and $R^3$ is a 4,6-bis-trichloromethyl-s-triazin-2-yl group, and n and m independently of each other, are one of the numbers 0 and 1,
said compound having an absorption in the range between about 300 and 500 nm.

2. A compound as claimed in claim 1, wherein $R^1$ is an unsubstituted phenyl radical or a phenyl radical substituted by 1 to 3 alkyl, alkoxy, phenyl, perhaloalkyl, nitro, cyano, carboxyl, carbonyl or diphenylamino groups.

3. A compound as claimed in claim 1, wherein $R^2$ is a hydrogen atom.

4. A compound as claimed in claim 1, wherein $R^1$ is a phenyl group substituted by 1 to 3 alkyl or alkoxy groups containing from 1–10 carbon atoms.

5. A compound as claimed in claim 1, wherein $R^1$ is a phenyl group substituted by 1 to 3 alkyl or alkoxy groups containing from 1–6 carbon atoms.

6. A compound as claimed in claim 1, wherein said compound has an absorption maximum between about 304 and 426 nm.

7. A compound as claimed in claim 1, wherein said compound has an absorption maximum between about 350 and 400 nm.

8. A compound as claimed in claim 1, wherein said compound has an absorption maximum at about 365 nm.

9. A process for preparing a compound of the formula I

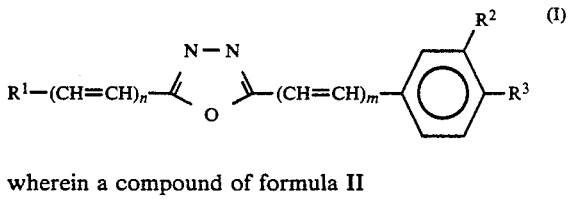

wherein a compound of formula II

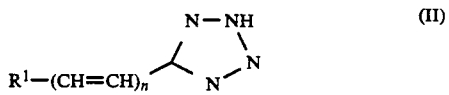

is reacted with a carboxylic acid halide of formula III

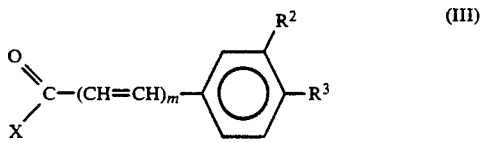

wherein
X is a halogen atom,
$R^1$ is one of a phenyl radical either unsubstituted or substituted by 1 to 3 alkyl, alkoxy, phenyl, perhaloalkyl, nitro, cyano, carboxyl, carbonyl or diphenylamino groups, a tolyl radical, a naphthyl radical, a biphenyl radical, a carbazolyl radical and a pyridyl radical,
one of $R^2$ and $R^3$ is a hydrogen atom and the other of $R^2$ and $R^3$ is a 4,6-bis-trichloromethyl-s-triazin-2-yl group, and n and m independently of each other, are one of the numbers 0 and 1.

10. A process as claimed in claim 9, wherein the reaction is carried out in a heterocyclic base as the reaction medium, at a temperature between about 50° and 150° C.

* * * * *